United States Patent [19]

Frost

[11] 4,400,575
[45] * Aug. 23, 1983

[54] METHANATION OF GAS STREAMS CONTAINING CARBON MONOXIDE AND HYDROGEN

[75] Inventor: Albert C. Frost, Congers, N.Y.

[73] Assignee: Union Carbide Corporation, Danbury, Conn.

[*] Notice: The portion of the term of this patent subsequent to Dec. 30, 1997 has been disclaimed.

[21] Appl. No.: 224,440

[22] Filed: Jan. 12, 1981

[51] Int. Cl.$^3$ ............................................. C10K 3/04
[52] U.S. Cl. ................................. 585/733; 48/197 R
[58] Field of Search ..................... 585/733; 48/197 R

[56] References Cited

U.S. PATENT DOCUMENTS

| | | | |
|---|---|---|---|
| 2,686,819 | 8/1954 | Johnson | 260/676 |
| 3,031,287 | 4/1962 | Benson et al. | 48/197 |
| 4,242,103 | 12/1980 | Rabo et al. | 48/197 R |
| 4,242,104 | 12/1980 | Frost | 48/197 R |
| 4,242,105 | 12/1980 | Frost | 48/197 R |

Primary Examiner—Thomas A. Waltz
Attorney, Agent, or Firm—Alvin H. Fritschler

[57] ABSTRACT

Carbon monoxide-containing gas streams having a relatively high concentration of hydrogen are pretreated so as to remove the hydrogen in a recoverable form for use in the second step of a cyclic, essentially two-step process for the production of methane. The thus-treated streams are then passed over a catalyst to deposit a surface layer of active surface carbon thereon essentially without the formation of inactive coke. This active carbon is reacted with said hydrogen removed from the feed gas stream to form methane. The utilization of the CO in the feed gas stream is appreciably increased, enhancing the overall process for the production of relatively pure, low-cost methane from CO-containing waste gas streams.

14 Claims, No Drawings

METHANATION OF GAS STREAMS CONTAINING CARBON MONOXIDE AND HYDROGEN

STATEMENT

The Government of the United States of America has rights pursuant to Contract No. DE-AC03-78CS 40177 awarded by the Department of Energy.

BACKGROUND OF THE INVENTION

1. Field of the Invention

The invention relates to the production of methane from carbon monoxide. More particularly, it relates to a methanation process capable of effectively utilizing the CO content of waste effluent streams employed as feed gas.

2. Description of the Prior Art

The production of low-cost methane as a replacement for natural gas has been the subject of considerable interest in light of the energy requirements of industrial societies throughout the world. The COthane process has been developed in response to such interest and concerns. It is particularly advantageous in that this process is capable of utilizing dilute carbon monoxide-containing gas streams without the necessity for the preliminary concentration that has precluded the use of such streams in conventional techniques for the production of methane from carbon monoxide and hydrogen. Thus, waste streams, such as the effluent from blast furnace operations, carbon black off-gas, underground coal gasification and the like, can be effectively utilized for the production of methane although such streams previously were unsuitable as useful sources of CO.

The COthane process is a cyclic, essentially two-step process in which a surface layer of active surface carbon is deposited on a catalyst and is then contacted with steam or hydrogen to convert the active surface carbon to methane and carbon dioxide. This essentially two-step process is repeated in cyclic operations without the need for regenerating the catalyst as a necessary additional step of the cyclic operation. Upon separation from carbon dioxide by conventional means, the methane is recovered in the form of a low-cost, relatively pure product, with the process effectively utilizing the carbon monoxide values of dilute carbon monoxide containing waste gas streams or other such sources of CO-containing feed gas for the process.

There is, of course, a desire in the art to continually improve the available methanation technology. With respect to the COthane process in particular, it is desirable to develop processing improvements and modifications to enhance the overall process, especially to broaden the scope of waste gas streams capable of being used as feed gas streams while maintaining or enhancing the effective CO utilization of the process as applied to such streams.

It is an object of the invention, therefore, to provide an enhanced process for the production of methane from carbon monoxide-containing gas streams.

It is another object of the invention to provide an improved process for the effective utilization of CO-containing waste gases for the production of methane.

It is a further object of the invention to provide a process for the production of methane from an enlarged scope of waste streams as suitable sources of CO for the indicated cyclic, essentially two-step methanation process.

SUMMARY OF THE INVENTION

The invention is based on the finding that the effective CO utilization of the COthane process can be appreciably enhanced, when the feed gas contains a relatively high concentration of hydrogen, by a pretreatment step in which hydrogen is removed in a recoverable form for use in the second step of the process. The beneficial results of this approach more than compensate for the necessary addition of a hydrogen removal step, thereby very appreciably enhancing the overall technical-economic feasibility of the COthane process for the production of methane from waste streams. The advantageous results of such removal and use of hydrogen from CO-containing gas streams serves to enlarge the scope of waste gas streams considered as suitable feed gas streams for the COthane process.

DETAILED DESCRIPTION OF THE INVENTION

The practice of the invention enables waste streams otherwise considered unsuitable for purposes of the COthane process to be effectively employed in the process with enhanced utilization of the CO content thereof. To avoid discarding to waste such carbon monoxide-containing gas streams, a process has heretofore been developed for the removal of hydrogen from said gas streams by a partial oxidation technique. Such a pretreatment step not only adds to the overall cost of the process, but destroys the hydrogen values of the gas streams with respect to the use thereof in the essentially two-step COthane process. The invention avoids the undesirable discarding to waste of a carbon monoxide-containing gas stream or the additional processing and expense of a partial oxidation of the hydrogen portion of the feed gas in a manner enhancing the technical and economic feasibility of employing the COthane process for the production of relatively pure, low-cost methane.

The COthane process to which the invention relates includes the passing of a carbon monoxide-containing gas stream over a suitable catalyst under conditions such that the carbon monoxide is decomposed to form carbon dioxide and active surface carbon, designated as C* and deposited as a surface layer on said catalyst, according to the reaction:

$$2CO \rightarrow CO_2 + C^*. \tag{1}$$

The carbon dioxide and inert gases present in the feed stream are vented from the surface layer of active surface carbon, which is thereafter converted to methane by contact with hydrogen or with steam as follows:

$$2C^* + 2H_2O \rightarrow CH_4 + CO_2. \tag{2}$$

The carbon efficiency of the process can be illustrated by the overall reaction (3) below that represents the total of reactions (1) and (2) as performed in the practice of the present invention:

$$4CO + 2H_2O \rightarrow 3CO_2 + CH_4. \tag{3}$$

Thus, 4 moles of CO are required for the production of one mole of methane in the stoichiometric relationship illustrated by reaction (3). The COthane process is capable of recovering methane in amounts representing at least about 50% of the stoichiometric amount and, in preferred embodiments, at least about 80% and up to nearly 100% of said stoichiometric amount. Upon separation from the accompanying $CO_2$ by conventional means, therefore, methane is recovered in the form of a low-cost, relatively pure product with the carbon values thus recovered being at least about 12.5% and up to nearly 25% of the carbon present in the carbon monoxide decomposed upon contact with the disproportionation catalyst.

Gas streams containing from about 1 to 100% by volume carbon monoxide can be utilized as the feed stream in the practice of the COthane process. The process is uniquely capable of utilizing carbon monoxide in gas streams not suitable for known methanation techniques because of relatively high concentrations of inert gases therein. Gas streams containing carbon monoxide in amounts of from about 5% to about 50% by volume and containing at least about 5% by volume of nitrogen represent sources of carbon monoxide not previously suitable for commercial methanation operations that are highly suitable for use in this process. The gas streams should, of course, be sufficiently free from catalyst poisons to ensure adequate catalyst lifetimes. Thus, sulfur impurities should be present in very low concentrations, e.g., less than 1 ppm, preferably less than 0.2 ppm. Conventional techniques are forming a part of this invention are available in the art for removing sulfur impurities as required. If hydrogen or water vapor is also present in the feed gas stream, it has been expected, based on thermodynamic calculations, that such gases would be converted, partially or completely, to methane by reaction with carbon monoxide or with active surface carbon under the reaction conditions. Only the carbon monoxide remaining after said reaction with hydrogen or water vapor would be expected to be decomposed to active surface carbon and carbon dioxide in accordance with reaction (1) above. For this reason, it was heretofore preferred that any hydrogen or water vapor be present in the feed gas stream in quantitites less than 10% by volume of the amount of carbon monoxide present in the gas stream. Gas streams containing larger amounts of hydrogen were either not considered for use as feed streams for the COthane process, or were pretreated by the indicated partial oxidation technique, or by a pre-methanation step, to remove said hydrogen prior to use in the process.

The carbon monoxide decomposition step, in which the carbon monoxide present in the feed gas stream is decomposed to form a surface layer of active surface carbon deposited on a disproportionation catalyst, effectively serves to concentrate the carbon values to be converted to methane, regardless of the carbon monoxide content of the feed gas stream. As a result, dilute carbon monoxide-containing gas streams can be readily employed in the cyclic, essentially two-step COthane process without the necessity for the prior concentration of the carbon monoxide as would be required in conventional techniques. The carbon dioxide formed as a result of carbon monoxide decomposition, together with the inert gases that may be present in the gas stream, is removed from the catalyst having the surface layer of active surface carbon values to be converted to methane. Such removal is readily carried out as an inherent part of the disproportionation step prior to said active surface carbon conversion in the second chemical step of the essentially two-step process of the COthane process. The use of a dilute carbon monoxide-containing gas stream as the feed gas for the process thus does not require the prior separation of the carbon monoxide content thereof from inert gases as would be required in conventional methanation techniques. This ability of the process to utilize dilute carbon monoxide-containing gas streams constitutes a major advance in the art, permitting the production of low-cost methane from gas streams not capable of practical utilization for the economic production of methane by presently available techniques.

The decomposition of carbon monoxide over a disproportionation catalyst is carried out at a reaction pressure of from about 1 to about 100 atmospheres and at a reaction temperature of from about 100° C. to about 350° C., preferably between about 200° C. and about 350° C. with space velocities frequently being from about 1000 to about 30,000 $hr^{-1}$. Since the most useful product of the carbon monoxide decomposition step is the solid surface layer of active surface carbons, it will usually be to no advantage to carry out the decomposition reaction at pressures much above atmospheric. The carbon monoxide-containing feed gas stream, pretreated in accordance with the invention, is passed over the catalyst for a time sufficient to deposit a surface layer of active surface carbon on the catalyst essentially without the formation of inactive coke thereon. Such inactive coke is not only itself inert under the methanation reaction conditions of the COthane process, but may tend to reduce the capacity of the catalyst to form active surface carbon in subsequent operations. For practical commerical applications of the process, such subsequent operations involve the use of the catalyst for the disproportionation of additional quantitites of CO and are desirably carried out at reaction temperatures above about 100° C. and preferably within said preferred range of from about 200° C. to about 300° C. or even higher up to about 350° C. It will be understood that said CO disproportionation or decomposition temperature refers to the average temperature of the reaction bed. It will also be understood by those skilled in the art that the particular reaction temperature pertaining to any given commercial application of the COthane process, or the modification thereof herein disclosed and claimed, will be subject to inevitable variations depending on the type of operation employed, e.g. fixed or fluid bed, and on the capability of temperature control equipment employed in such commercial application of the process. The reaction temperature may exceed the indicated preferred temperature limits on a transitory basis without departing from the scope of the process or of this invention although, for enhanced economic and technical practicability of commercial applications, the average reaction bed temperature should desirably be within the preferred range indicated above, i.e., from about 100° C., most preferably from about 200° C. up to about 350° C. At higher temperatures, the suitability of the catalyst for use in the cyclic, two-step COthane process is diminished so that the overall efficiency of the process is adversely effected, and the cost thereof increased, at such less favorable operating conditions.

It should be noted that the active surface carbon formed in the practice of the COthane process is quite distinct from the inactive coke formed if the carbon monoxide decomposition is allowed to proceed beyond the maximum level of active surface carbon deposition. Such inactive coke is known in the art as an undesired potential deposit on catalyst surfaces from carbonaceous feeds employed in various methanation operations. Such coke has essentially the reactivity of graphitic carbon. Its reaction with steam, for example, requires temperatures in the range of from about 600° C. to about 1000° C. This reaction, which is the well-known water gas reaction, produced CO and H2 as its principal products. The active surface carbon of the COthane process and of the present invention, on the other hand, reacts with steam or hydrogen at appreciably lower temperature levels to provide methane as its principal product, as is shown in equation (2) above. While the prior art is concerned with the avoidance of the undesired deposition of inactive coke on catalytic surfaces, the COthane process and the present invention utilize the deposition of active surface carbon, without formation of inactive coke, to produce methane by the low-cost process as described herein.

The amount of active surface carbon deposited will depend upon the surface area of the disproportionation catalyst and the operating conditions employed. Relatively low temperatures and the shortest possible residence time tend to favor the formation of the active surface carbon. Under some circumstances, particularly at higher temperatures within the operable range or with a very long residence time, the presence of CO in the gaseous effluent denotes a relatively short demarcation point between the deposit of the desired active surface carbon and the undesired deposition or other formation of inactive coke on the surface of the catalyst. In determining the amount of active surface carbon that can be deposited on the catalyst, therefore, the point at which CO breakthrough occurs can be taken as a practical indicator of the maximum level of active surface carbon deposition. It will be understood, however, that said maximum level of deposition must be determined, for any particular embodiment, by the particular operating conditions employed, the specific catalyst utilized and the available surface area of the catalyst as applied in such embodiment.

The COthane process utilizes a catalyst capable of catalyzing the disproportionation of carbon monoxide. The transition metals including and to the left of nickel in the third row of the Periodic Table; including and to the left of rhodium in the fourth row thereof; and including and to the left of iridum in the fifth row thereof are capable of catalyzing said disproportionation. Preferred catalysts include nickel, cobalt, iron, ruthenium, rhenium and alloys thereof, with nickel and cobalt being most preferred on an overall technical-economic basis. For purposes hereof, it will be understood that the catalyst shall include the metallic form, the oxide form, or any other suitable form of the particular catalyst employed. As the active surface carbon will be deposited in a surface layer while assuring that the decomposition reaction does not proceed to the point of inactive coke formation, a high catalyst surface area is advantageous to achieve a high surface carbon loading, enhancing the economics of the process. The catalyst employed will preferably have a surface area of at least about 10 m²/gr, with surface areas of at least about 25 m²/gr being more preferred. In some embodiments, the catalyst may have an even higher surface area, i.e., of at least about 50 m²/gr., it being appreciated that such high surface areas contribute to the attractiveness of the invention on an overall technical and economic basis. It will also be appreciated that the catalyst will generally be employed in combination with catalyst support additives and/or binding agents to assure that the catalyst has and maintains a desired combination of activity, capacity and stability for use in practical fixed or fluid bed commercial operations. It will also be understood that the surface area of the catalyst, as referred to herein, relates to the B.E.T. surface area of the catalyst composition measured after the combination of the catalyst with such additives or agents and after reduction of the catalyst to its active state.

For the economic production of methane in practical commercial operations, it is highly desirable that the catalyst be capable of use in the essentially two-step, cyclic, low cost COthane process without the need for regeneration following each reaction cycle. Furthermore, the catalyst should advantageously be capable of effective continued use in the cyclic, two-step process over as long a cycle period as possible prior to regeneration to enhance the economic feasibility of the process in such commercial operations. The catalyst will, in particularly preferred embodiments, be employed essentially in its metal state and will be taken from especially preferred catalysts, including nickel, cobalt, ruthenium, rhenium and alloys thereof, with nickel and cobalt being most preferred on an overall technical-economic basis to enhance the cyclic feature of the essentially two-step COthane process. It will be understood by those skilled in the art that such catalysts, in their metal state, are not generally available in a totally pure form but may contain small amounts of oxygen. The especially preferred catalysts enhancing the cyclic, two-step COthane process will be substantially in the metal state rather than in oxide form. It will be noted that iron is not included among the especially preferred catalysts for practical commercial operation of the two-step, inherently cyclic process, since iron is considerably less reactive to CO in the initial disproportionation step than is the most preferred nickel and cobalt catalysts and tends to form an inactive oxide. It may also be necessary to convert the iron catalyst from the oxide form to iron metal form as a separate and necessary additional step of the cyclic process. Such a requirement would, of course, change the process from one having two essential chemistry steps, repeated on a cyclic basis, to a process having three essential chemistry steps. The economic and technical advantages of the inherently cyclic, two-step process would not be realized, therefore, in commercial operations in which iron, in oxide form, is employed as the disproportionation catalyst.

As indicated above, inert gases present in the carbon monoxide-containing feed gas stream, together with gases formed during carbon monoxide decomposition, are vented from the reaction zone in which a surface layer of active surface carbon is deposited on the disproportionation catalyst. As a result, the carbon values in the carbon monoxide that are to be converted to methane are inherently separated from said inert gases. No prior concentration of the carbon monoxide present in dilute carbon monoxide-containing gas streams, and no separation of said carbon monoxide from inert gases such as nitrogen and argon present in said gas streams, are required. It is such requirements and the cost thereof that effectively preclude the use of dilute carbon monoxide-containing gas streams in prior art methanation techniques. The COthane process and this invention achieve, in effect, such concentration essentially without a cost penalty compared to alternative processes that utilize gas streams containing a relatively high proportion of carbon monoxide therein to avoid the necessity for employing a prohibitively costly cryogenic or other separation of inerts. The process is particularly advantageous and achieves a major advance in the art in permitting the methanation of dilute carbon monoxide-containing gas streams and a relatively high proportion of inerts, e.g., the indicated gas streams containing from about 5% to about 50% by volume carbon monoxide.

The conversion of active surface carbon to methane is accomplished, in the practice of the invention, by contacting the surface layer of said carbon with hydrogen recovered from the feed gas. Methane is formed in accordance with the reaction:

$$C^* + 2H_2 \rightarrow CH_4. \qquad (4)$$

The hydrogen requirements of reaction (4) are supplied by passing the carbon monoxide-containing feed gas stream, having a hydrogen concentration of at least about 50% by volume based on, or relevant to, the volume of CO present in said feed gas stream, through a hydrogen separation unit or zone to separate said hydrogen in a removable form therefrom.

As the modified COthane process of the invention utilizes reactions (1) and (4) above, after pretreatment of the feed gas for said hydrogen separation, it will be appreciated that two moles of CO are required for the production of one mole of methane. By contrast, previous consideration was given to the use of hydrogen for active surface carbon conversion with the hydrogen requirements of reaction (4) being supplied from the CO content of the feed gas via the very well known water shift reaction. In such an approach, four moles of CO are required for the production of one mole of methane as in the embodiment in which stean is employed for carbon conversion as represented by reaction (3) above. The use of steam was preferred over the use of hydrogen because of the costs associated with the generation of hydrogen. In the embodiments utilizing steam, the $CO_2$ formed can readily be separated from the methane by known commercial techniques, such as the Benfield aqueous alkaline scrubbing process, and the Shell Sulfinol and Allied Chemical Selexol solvent extraction processes.

The conversion of active surface carbon to methane by reaction with hydrogen removed from the feed gas is carried out under the same general conditions employed when steam is employed for such conversion. Thus, reaction temperatures of from about 100° C. to about 400° C. may be employed, with temperatures within the range of from about 200° C. to about 350° C. being generally preferred. Reaction pressures of from about 1 to about 100 atmospheres may be employed.

It has been determined that the presence of hydrogen in a CO-containing feed gas stream will not, at low pressure and with a very short residence time for the disproportionation step, react to a significant degree with the active surface carbon as it is being deposited on the catalyst. Quite surprisingly the CO utilization of the COthane process is found actually to increase in practical embodiments of the process from about 19-20% to about 25%. To achieve this desirable result, it is necessary to employ a relatively low disproportionation pressure, e.g., about 1-10 atmospheres, preferably about 1-4 atmospheres. It is also necessary to maintain a relatively short residence time in the disproportionation step i.e., a residence time far less than that in which of inactive coke is formed. Under such conditions, the presence of hydrogen is the feed gas contibutes to the formation of active surface carbon without the formation of inactive coke or an appreciable amount of methane that is undesired during the disproportionation step.

Thus, the presence of hydrogen in the feed gas is not disadvantageous as previously believed, at low pressure, short residence time conditions for the disproportionation step. It is nevertheless desirable, and it has been found, that the CO utilization of the COthane process can be further enhanced to a very appreciable extent by the practice of the invention. In the modification of the COthane process that constitutes the invention, hydrogen is removed from the feed gas in a recoverable form and is thereafter used for reaction with the active surface carbon to form product methane. Despite the additional hydrogen removal pretreatment step required in the process of the invention, the overall process for the production of relatively pure, low-cost methane is enhanced by the appreciable enhancement in CO utilization achieved by the invention. As used herein, the term "CO utilization" will be understood to mean the ratio of the amount of methane produced/the amount of CO consumed. It has been found that the CO utilization can be increased from about 20% to about 40% or more by means of the present invention as compared with a conventional COthane process operation. By contrast, the enhancement of the COthane process unexpectedly by the presence of hydrogen retained in the feed gas, and used under the conditions indicated above, was from about 20% to about 25%.

For purposes of the invention in enhancing the overall COthane process, the feed gas stream from which hydrogen is separated for use in the second step of said process should contain a relatively large amount of hydrogen relative to the CO content of the stream. Thus, the hydrogen content should be at least about 50% by volume based on the volume of CO present in the stream. It will be appreciated that it will be necessary to supplement the recovered hydrogen so used for conversion of the active surface carbon with steam or a steam-containing gas when the hydrogen content of the feed gas stream is less than 100% by volume relative to the CO content of the feed gas steam.

The advantageous results of the present invention are achieved under two sets of conditions distinguishing from the conditions under which the presence of hydrogen has been found desirable in the feed gas to the disproportionation step. In one embodiment, the recovered hydrogen can be employed for conversion of active surface carbon to methane under reaction pressure conditions greater than those found necessary or desirable to prevent methane formation in the disproportionation step of the alternate discovery, with such higher pressure extending up to about 100 atmospheres. In another embodiment, the recovered hydrogen can also be employed at the lower pressures of the alternate approach but with a longer residence time for the active surface carbon step so that said hydrogen and active surface carbon react to form the desired methane product. In the alternate approach wherein hydrogen is left in the feed, the active surface carbon deposition step is carried out quickly so as to avoid such methane formation. Those skilled in the art will appreciate that the pressure and residence time requirements can be adjusted in particular embodiments so that the desired methane product is formed in such embodiments. The use of conversion pressures of five or more atmospheres has been found desirable, with a range of from about 100 to 500 psi being convenient. It will be appreciated that the carrying out of the active surface carbon conversion step at elevated pressures, with or without the supplementing of the hydrogen with steam, is very useful as the methane product is thereby generated as a high-pressure product gas stream without the need for expensive compression equipment and high energy consumption for bringing the product to pipeline pressure conditions.

In the practice of the invention as in the conventional practice of the COthane process using feed gas streams containing only relatively small amounts of hydrogen in the gas stream, the disproportionation catalyst will typically be mixed with a catalyst support additive or with binders to assure that the catalyst has a desired combination of activity, capacity and stability. In the absence of such additives and/or binders, nickel, for example, is relatively unstable and tends to agglomerate and sinter with resultant reduction of its surface area.

It is within the scope of the invention to employ any available support additive material capable of supporting and/or dispersing the catalyst, so as to prevent agglomeration and sintering thereof, to enhance the activity and capacity of the catalyst in continuous commercial operations. Such support additives will generally be employed in varying amounts ranging from about 0.1% to about 50% by weight of additive based on the weight of catalyst composition mixture of catalyst and additive. Examples of suitable additives are zirconia, thoria, alumina, silica and mixtures thereof, although various other materials, such as rare earth oxides, may be employed for the indicated catalyst support purposes. In particular embodiments of the invention, the additive is employed in an amount within the range of from about 3% to about 15% by weight based on the weight of the catalyst composition mixture. Zirconia, alumina and silica are preferred catalyst support additives with zirconia being generally most preferred.

It will be understood that various combinations of such support additive materials, with or without binding agents, may be employed to achieve desired support and/or dispersion of the disproportionation catalyst employed in particular embodiments of the process of the invention. For example, it has been found advantageous to employ a combination of zirconia and alumina support additives. Each additive may preferably be employed in an amount within the range of from about 3% to about 30% by weight of the catalyst composition mixture of catalyst and additive with the combination being employed in an amount up to about 50% by weight based on the weight of said catalyst composition. As indicated above, nickel is the generally preferred catalyst, with the surface area of the catalyst being generally at least about 10 $m^2/gr$, and preferably at least about 25 $m^2/gr$, more preferably at least about 50 $m^2/gr$. Binding agents, if employed, will generally be mixed with the catalyst composition in an amount within the range of from about 5% to about 40% by weight of such binding agent based on the total weight of the catalyst composition-binder mixture. Various binding agents known in the art may be employed in a conventional manner as will readily be appreciated by those skilled in the art. Boehmite alumina, a hydrous aluminum oxide, and colloidal silica are convenient readily available binders.

While various catalyst-support additive combinations suitable for the purposes of the COthane process and of the invention may readily be determined by those skilled in the art, it has been found particularly convenient to employ a coprecipitated mixture of catalyst and catalyst support additive. Thermally stable coprecipitated catalysts useful for methanation reactions have heretofore been known in the art as evidenced, for example, by the Hansford patent, U.S. Pat. No. 3,988,263 that relates to combinations of alumina with catalytic materials such as nickel. The catalyst support additive, in such embodiments, constitutes generally the hydroxide or carbonate form thereof coprecipitated with the hydroxide or carbonate of the catalyst material prior to the reduction of said catalyst hydroxide or carbonate to the active catalyst state. For purposes of the present invention, the catalyst should comprise from about 50% to about 99% of the catalyst composition mixture of catalyst and additive. Nickel and cobalt are preferred catalysts, with silica being the preferred catalyst support additive although it will be appreciated that alumina, zirconia or other suitable support additives can also be employed.

While the COthane process necessarily includes two basic chemistry process steps, repeated on a cyclic basis, it will be understood that various processing steps, or unit operation steps, may be carried out incidental to said two COthane process steps and the hydrogen separation pretreatment step of the invention. Thus, it was noted above that pretreatment of the feed may also be employed to remove sulfur impurities. In addition, by-product carbon dioxide formed during conversion of active surface carbon with steam in accordance with reaction (2) as a result of the use of steam to supplement the separate hydrogen is separated from product methane by conventional techniques. It will be understood by those skilled in the art that various other processing steps incidental to the heart of the present invention may be employed in practical applications of the invention. Accordingly, small adjustments in reaction temperature may be made, as by heating or cooling the reaction zone, and a purge gas at a desired temperature, e.g., about 240° C., may be passed through said zone to achieve a desired cooling effect. It will also be understood that, during repeated cycles of the cyclic, basically two-step COthane process, the disproportionation catalyst becomes coated with carbon that eventually reduces th efficiency of the catalyst to the point where catalyst regeneration becomes necessary or desirable. Oxidative regeneration can be employed to burn off said carbon so as to regenerate the catalyst for subsequent use in the cyclic, two step methanation process of the invention. Such regeneration can be conveniently carried out in situ in the reaction zone.

The beneficial effects of the present invention can be demonstrated using a feed gas stream having a hydrogen concentration particularly high in relation to the CO concentration, e.g., a cooled carbon black off-gas. Such a gas stream contains about 15% CO, 15% $H_2$, 2% $CO_2$ and 68% $N_2$. By passing such a gas stream through a cryogenic distillation column for the separation of hydrogen therefrom and thereafter using the recovered hydrogen in the active surface carbon conversion step, the indicated increase of CO utilization from about 20% for a conventional COthane operation using a feed essentially without hydrogen and employing steam for the carbon conversion step, to more than 40%. In an illustrative example, a nickel catalyst was employed, 150 psig steam was employed in the carbon conversion step of the conventional COthane process and 150 psig hydrogen removed from the carbon black off-gas fluid stream in the pretreatment step of the invention was used for the carbon conversion step thereof. Thus, the ml of methane produced per gm of catalyst per cycle at least doubled from about 4–5 to about 9–10 or more in the course of operations carried out on a cyclic basis employing runs of more than 100 cycles between catalyst burn off for regeneration purposes. An increase in CO utilization of from about 25% for the processing of carbon black off-gas without a hydrogen removal/reuse for hydrogeneration sequence to the about 40% or more for the processing of the gas with said sequence of the invention results in an increase in the methane production rate by a factor of 40/25 or 1.6, while the costs were increased by only the expense of the hydrogen removal step. The greater CO utilization is found to more than compensate for the necessary hydrogen removal step, so that the overall process is enhanced by the practice of other invention. It should be noted, in this regard, that there is a minor reduction in cost in the practice of the invention as a result of the reduced requirements for the $CO_2$ removal unit for treating the effluent from the hydrogeneration step of the invention as compared with the need for a larger $CO_2$ removal unit when steam is employed for the active surface carbon conversion step.

Those skilled in the art will appreciate that the pretreatment step of the invention, i.e. the removing of hydrogen in a recoverable form from the feed gas stream, can be carried out using techniques available in the art but not heretofore deemed applicable to the carrying out of the Cothane process. Thus, the feed gas stream can be passed to a cryogenic distillation column, as indicated above, to separate hydrogen as an overhead material from the CO and nitrogen or other inert components of the feed gas. In a typical illustrative example, a feed gas stream at about 15 psia can be compressed to about 190 psia and passed to the cryogenic distillation column from which hydrogen is removed overhead at about 170 psia. After heat exchange with the incoming compressed feed gas stream, the $Co/N_2$ bottoms material from the column is available at about 40 psia as a suitable treated feed gas stream for passage to the disproportionation reactor for use in the first step of the Cothane process. The hydrogen content of the feed gas can be recovered at about 98% by such a cryogenic pretreatment step. The recovered hydrogen can be used in place of steam in the second step of the Cothane process. In this regard, it should be noted that the recovery of hydrogen at elevated pressure is advantageous for the desirable production of methane at high pressure, thereby reducing or eliminating the need for expensive compression equipment for the product gas steam.

Another technique available in the art that can be applied to the hydrogen removal pretreatment step of the invention is the well-known pressure swing adsorption process. This process has been described in the Wagner patent, U.S. No. 3,430,410, the Fuderer et al patent, U.S. No. 3,986,849, and numerous other references available in the art. The feed gas to be pretreated is passed to an adsoption bed at elevated pressure so that hydrogen is passed through and recovered, while CO, $N_2$ and other inert materials are retained on the adsorbent material in the bed. Upon subsequent depressurization, the adsorbed materials can be removed from the bed, which can then be repressurized for further adsorption when passage of additional quantities of the feed gas stream through the adsorption bed at elevated pressure. As the references to such technology clearly teach, the pressure swing adsorption process can advantageously be carried out in multiple adsorption bed systems each of which undergo, in sequence, the processing cycle of pressurization, high pressure adsorption, depressurization, low pressure purge and repressurization as is well known in the art. In an illustrative example of this technique, a feed gas steam containing 15% by volume CO, 15% $\frac{1}{2}$ and the balance nitrogen, can be pretreated in a pressure swing adsorption unit at about 200 psia for adsorption, with about 20 psia waste pressure, to recover about 70% of the hydrogen from the feed gas steam at about 99.9% purity. As with the cryogenic distillation approach, the recovery of hydrogen at relatively high pressure for use in the second step of the Cothane process is advantageous for the desirable production of methane in mid second step and high pressure.

As indicated above, the present invention enables two moles of CO to be converted to one mole of product methane by the Cothane process approach. The CO utilization of the process was thus increased from what 20% for the conventional practice of the Cothane process to about 40% or more. It has actually been observed in some instances, however, that CO utilizations of about 60% are obtained in the practice of particular embodiments of the invention. This is believed to result from the reaction of the recovered hydrogen used in the second step of the Cothane process not only with the active surface carbon referred to above, but with CO that is chemi-sorbed on the catalyst. A theoretical maximum CO utilization of 100% is obtainable when hydrogen reacts directly with the chemi-sorbed CO, as indicated by the reaction: (5) CO (chemi)+$3H_2O$. The unexpected CO utilization utilization was indicative of some CO chemi-sorption conversion to methane in addition to active surface carbon conversion that took place with an illustrative feed gas steam comprising a cooled carbon black off-gas containing about 15 vol. % $CO_2$ and about 65 vol. % $N_2$ on a water-free basis. Such an off-gas stream is one of the most promising effluent waste streams available for the practice of the Cothane process.

As heretofore indicated, the CO disproportionation step of the process is preferably carried out at a temperature of from about 200° C. to about 350° C., a temperature of about 310° being particularly convenient in practical embodiments of the invention. At such a temperature of about 310° or higher, it appears that the major portion of the CO content of the feed gas stream is decomposed to from active surface carbon that is deposited on the catalyst, with a very small amount of CO being chemi-sorbed on the catalyst at the decomposition temperature. On the other hand, the use of disproportionation temperatures of from about 200° C. to about 240° C., or temperatures below this range, appears to result in the formation of some active surface carbon, but with the chemi-sorption of a major portion of the CO content of the feed stream. This would, of course, produce the CO utilization of the process unless said CO chemi-sorbed on the catalyst is reacted with hydrogen per reaction (5) above to produce methane in addition to that produced in accordance with reaction (4) above. As the hydrogen available is generally limited, in practical applications, to that recovered from the feed gas stream in the pretreatment step of the invention, the embodiment in which the carbon monoxide decomposition temperature is from about 200° C. to about 240° C. is most advantageously employed when the hydrogen concentration is at least 300% by volume based on the amount of carbon monoxide present in the feed gas stream. In such a case, it will be understood that the amount of hydrogen that can be removed from the feed gas stream in the pretreatment step and reused in the second step of the Cothane process will be sufficient to supply the requirements of reaction (5) pertaining to chemi-sorbed carbon monoxide. Those skilled in the art appreciate, based on the unexpected finding of a very significant additional increase in CO utilization as discussed above, that at various other conditions, the amount of chemi-sorbed CO present on the catalyst, in addition to active surface carbon, will likewise vary. At an intermediate CO decomposition temperature of about 270° C., for example, a greater balance of active surface carbon and chemi-sorbed CO is likely to form than it either of the temperature extremes referred to above. At such intermediate temperature, therefore, the CO utilization will be enhanced if the stream being treated is one having a hydrogen concentration of from about 200 to 300% based on the amount of carbon monoxide present in the feed gas stream. In this manner, the active surface carbon and the chemi-sorbed CO that may be present on the catalyst can both be converted to product methane, leading to the very significant enhancement in the CO utilization of the process as disclosed herein.

The invention will be seen to represent a very important advance in the development of the COthane process. By enhancing significantly the CO utilization of the process, the invention increases the prospects for the use of the COthane process in practical commercial operations for the production of low-cost methane from co-containing waste gas streams.

Therefore, what is claimed is:

1. A cyclic process for the production of methane from carbon monoxide-containing gas streams comprising:
   (a) passing a carbon monoxide-containing gas stream having a hydrogen concentration of at least about 50% by volume, based on the volume of CO present in said stream, through a hydrogen separation unit to separate said hydrogen in a recoverable form from said gas stream;
   (b) passing the thus-preheated carbon monoxide-containing gas stream over a catalyst present in a metal state and capable of catalyzing the disproportionation of carbon monoxide at a pressure of from about 1 to about 100 atmos and a temperature of from about 100° C. to about 350° C., said carbon monoxide thereby being decomposed to form carbon dioxide and an active surface carbon that is deposited on said catalyst, said gas stream being passed over the catalyst for a time sufficient to deposit a surface layer of said active surface carbon on the catalyst essentially without the subsequent formation of inactive coke thereon;
   (c) contacting said layer of active surface carbon deposited on the catalyst with said hydrogen removed from the carbon monoxide-containing gas stream of step (b) above at a pressure of from about 1 to about 100 atmos and a temperature of from about 100° C. to about 400° C. for a period of time sufficient to convert said active surface carbon to methane; and
   (d) passing additional carbon monoxide-continuing gas through said pretreatment hydrogen separation zone, and over said catalyst from step (c) and repeating steps (b) and (c) on a cyclic basis, whereby relatively pure methane can conveniently be produced from carbon monoxide-consuming gas streams containing appreciable quantities of hydrogen on a cyclic basis, the use of said hydrogen removed from the feed gas for the conversion of the active surface carbon to methane enhancing the utilization of the CO content of said feed and the overall process for the production of relatively pure, low-cost methane therefrom.

2. The process of claim 1 in which said feed gas stream contains from about 5% to about 50% by volume carbon monoxide.

3. The process of claim 1 in which said carbon monoxide decomposition temperature is from about 200° C. to about 350° C.

4. The process of claim 1 in which said conversion of active surface carbon by hydrogen is at a temperature of from about 200° C. to about 350° C.

5. The process of claim 1 in which the hydrogen content is less than 100% by volume relative to the CO content of the feed gas stream, and including supplementing the recovered hydrogen used for conversion of the active surface carbon with steam or a steam-containing gas, said steam reacting with the active surface carbon to produce methane and carbon dioxide.

6. The process of claim 5 in which said surface active conversion is carried out at a pressure of from about 100 to about 500 psi, the use of high pressure steam permitting the generation of a high-pressure product gas steam without the need for expensive compression equipment and high energy consumption.

7. the process of claim 1 in which said carbon monoxide-containing gas stream is passed to a cryogenic distillation column as said hydrogen separation unit.

8. The process of claim 1 in which said carbon monoxide-containing gas stream is passed to a pressure swing absorption unit for said separation of hydrogen from the CO-containing gas stream.

9. The process of claim 6 in which said carbon monoxide decomposition temperature and said temperature for conversion of active surface carbon are each from about 200° C. to about 350° C.

10. The process of claim 1 in which said carbon monoxide decomposition temperature is from about 200° C. to about 240° C.

11. The process of claim 10 in which said hydrogen concentration is at least about 300% by volume based on the amount of carbon monoxide present in the feed gas stream, said hydrogen being employed for reaction with CO chemi-sorbed on said catalyst at the decomposition temperature in addition to use for said conversion of active surface carbon deposited on said catalyst to product methane.

12. The process of claim 1 in which the hydrogen concentration is about 100% by volume based on the amount of carbon monoxide present in the feed gas system.

13. The process of claim 12 in which said feed gas stream comprises carbon black off-gas.

14. The process of claim 13 in which said carbon monoxide decomposition temperature is from about 200° C. to about 350° C.

* * * * *